United States Patent [19]

Krause et al.

[11] Patent Number: 5,602,449
[45] Date of Patent: Feb. 11, 1997

[54] MOTOR CONTROLLED SURGICAL SYSTEM AND METHOD HAVING POSITIONAL CONTROL

[75] Inventors: Kenneth W. Krause, Sandown, N.H.; Douglas D. Sjostrom, Reading, Mass.

[73] Assignee: Smith & Nephew Endoscopy, Inc., Andover, Mass.

[21] Appl. No.: 420,243

[22] Filed: Apr. 11, 1995

Related U.S. Application Data

[63] Continuation-in-part of Ser. No. 135,297, Oct. 12, 1993, abandoned, which is a continuation-in-part of Ser. No. 867,871, Apr. 13, 1992, Pat. No. 5,270,622.

[51] Int. Cl.$^6$ .............................. H02P 6/20; H02P 6/24; A61B 17/32
[52] U.S. Cl. ............................................ 318/254; 128/755
[58] Field of Search ..................... 128/751, 755; 604/19, 22; 606/53, 79, 118, 167–171, 174, 180; 318/138, 254

[56] References Cited

U.S. PATENT DOCUMENTS

| | | |
|---|---|---|
| Re. 34,556 | 3/1994 | Sjostrom et al. . |
| 4,200,106 | 4/1980 | Douvas et al. . |
| 4,345,192 | 8/1982 | Kohzai et al. .................. 318/592 |
| 4,403,179 | 9/1983 | Kohzai et al. .................. 318/632 |
| 4,705,038 | 11/1987 | Sjostrom et al. . |
| 4,867,155 | 9/1989 | Isaacson . |
| 4,995,877 | 2/1991 | Ams et al. . |
| 5,030,900 | 7/1991 | Kono et al. .................. 318/592 |
| 5,048,538 | 9/1991 | Terwilliger et al. .................. 128/754 |
| 5,171,245 | 12/1992 | Cezana . |
| 5,207,697 | 5/1993 | Carusillo et al. . |
| 5,222,953 | 6/1993 | Dowlatshahi .................. 606/15 |
| 5,269,794 | 12/1993 | Rexroth . |
| 5,270,622 | 12/1993 | Krause . |
| 5,403,276 | 4/1995 | Schechter et al. .................. 604/22 |

FOREIGN PATENT DOCUMENTS

PCT/US94/08124  2/1995  WIPO .

*Primary Examiner*—Bentsu Ro
*Attorney, Agent, or Firm*—Fish & Richardson P.C.

[57] ABSTRACT

A surgical system, adapted to operate with at least one surgical device, has a handpiece containing a motor which is adapted to receive the surgical device. The surgical device is driven through a continuum of positions by the motor output shaft. A controller microprocessor controls the operation of the system. The motor has sensors for generating electrical position signals and the controller is responsive to input signals for defining both a stop position and a reversal position for the surgical device. As a result, the controller initiates operation of the surgical device at the so called stop position and stops operation of the surgical device so that it comes to rest substantially at the stop position. In an oscillatory mode of operation, the controller also forces reversals to occur solely at a reversal position dictated by the system, under the control of the user. In connection with an arthroscopic cutting device, the control enables the surgeon to control, for example, the opening of the aperture through which tissue and fluids are removed from the surgical site during the reversal and start/stop conditions.

30 Claims, 9 Drawing Sheets

MOTOR CONTROLLED SURGICAL SYSTEM AND METHOD HAVING POSITIONAL CONTROL

CROSS REFERENCE TO RELATED APPLICATIONS

The present application is a continuation-in-part of application Ser. No. 08/135,297, filed Oct. 2, 1993, now abandoned, which is a continuation-in-part of application Ser. No. 07/867,871, filed Apr. 13, 1992, now U.S. Pat. No. 5,270,622, both of which are incorporated by reference herein.

BACKGROUND OF THE INVENTION

This invention generally relates to motor driven surgical systems, and, more particularly, to a system for controlling the relative positions of components of an all digital motor controlled surgical system.

Digital speed control systems for controlling the rotational speed of brushless motors used, for example, with arthroscopic cutting devices are now well known.

These brushless motor controlled devices typically adapt to a surgical assembly and use an all digital well defined system such as that disclosed in U.S. Ser. No. 135,297 and U.S. Pat. No. 5,270,622, referred to above. They provide excellent control over the rotational speed and position of the motor armature, which enables precise and accurate control of the surgical assembly through an appropriate gear reduction between motor and assembly. Such digital control systems provide an advancement over the prior analog controlled systems using, typically, brushless motors.

In all of these motors, however, the relative position of the rotatable driven surgical member to the fixed housing in which it rotates, and in particular, the relative opening of, for example, a cutting aperture at the distal tip of the surgical device is unknown. In this respect, both brushless (all digital) and brush motors suffer the same difficulty, in that the nature of the aperture is unknown to the control system and, in particular, there was no way of maintaining any fixed relationship, known to the control system, between the rotatable portion of the removable rotary tip of the surgical device and its enclosing fixed housing.

It is therefore an object of the invention to improve the control over the relative location of the rotational portion of the driven surgical member, and in particular, to provide an apparatus which enables the physician to improve the efficiency and effectiveness of an arthroscopic cutting device and the accuracy with which the cutting process proceeds.

It is a general object of this invention to advance the state of the art in the control of brushless motors, particularly in connection with controlled arthroscopic cutting devices.

Another object of this invention is to provide an all digital motor controlled surgical cutting device having improved cutting effectiveness, accuracy, and response repeatability.

Another object of the invention is to provide an improved motor controlled system which has particular application in surgical procedures.

Yet another object of the invention is a method and apparatus which accurately and repeatably control motor driven surgical tools.

SUMMARY OF THE INVENTION

In keeping with these objects, and others which will become apparent hereinafter, the invention employs an all digital surgical control system for a brushless motor. The system comprises a digital signal processor for supplying command signals indicative of a desired motor operation. The processor or controller generates, for each phase of motor drive, and in response to the external control signals, a digital commutation signal to rotate the armature. A digital pulse width modulated signal having a duty cycle established by the control signals controls armature rotational speed.

The system further has a switching element, for example a multi-phase bridge, in digital communication with the controller. The bridge is operative for generating, for each phase, and in response to each commutation signal and each pulse width modulated signal, a digital two-state control signal having an on-state which lasts for the duration of the pulse width modulated signal.

The system still further has elements in digital communication with the controller, for generating, as the motor rotates, position sensor signals indicative of armature position. The controller is operative for processing the position sensor signals to generate a digital signal indicative of the actual armature rotational speed.

The invention features, in one aspect, shutting down or stopping the motor, either at the end of an oscillatory mode wherein the motor is constantly and automatically reversed, or in a continuous mode, at the end of a cutting cycle, so that the driven portion of a surgical device stops at a known and specified location.

In a particular aspect of the invention, a surgical system is adapted to operate with at least one surgical device. The surgical system has a handpiece containing a motor and the motor is adapted to receive and drive the surgical device. The surgical device is driven through a continuum of positions by the handpiece under the control of a controller. The surgical system features sensors in the motor for generating electrical signals indicative at least of a motor drive relative position, and a controller which is responsive to the relative position electrical signals for identifying a current position of the motor drive relative to a motor drive initial position. The system further features a position identifier for identifying to the controller a start-stop position for the driven surgical device, that is, a position at which to leave the surgical device when it is stopped. A stop switch is electrically connected to the controller, and the controller is responsive to actuation of the stop switch for stopping driven movement of the surgical device at substantially the start-stop position.

In various aspects of the invention, the motor controller can operate in either an open loop or a closed loop fashion. In one particular open loop embodiment, a manual switch is provided and the controller is responsive to actuation of the manual switch for marking the position of the driven surgical device at the start-stop position. Prior to operation of the manual switch, the driven portion of the surgical device can be slowly incremented until it reaches a desired start-stop position.

In a closed loop mode of operation, the invention further features a sensor element secured to the surgical device for causing the generation of an electrical signal which identifies a device determinative position when the surgical device is positioned substantially at the determinative position, and the controller, in response at least to the generated electrical signal can stop the driven member of the surgical device at substantially a previously determined start-stop position.

In the closed loop mode of operation, in some embodiments, the surgical device will be one-way keyed to the handpiece, where the sensing elements for providing the position electrical signals are located.

Since, in typical systems, the controller does not know the absolute position of the surgical device, it relies upon the relative position of the motor with respect to an original position. In these instances, the controller tracks the position of the motor armature relative to the original position of the armature when the manual switch was operated identifying the original (start-stop) position. If at the time a stop signal is given, the armature is rotating at a speed above a given threshold, the controller preferably waits (and optionally actively decelerates the driven member) until the speed decreases to a threshold value before instituting a stop procedure designed to stop the driven surgical member at the start-stop position.

In accordance with the invention, there is also provided a second mode of operation, in addition to the continuous mode of operation generally described above, in which the drive motion of the motor oscillates, the motor first being driven in one direction and then in the other direction. In this mode of operation, the invention provides for the option of adding an oscillatory or reversal stop position at which reversal of direction takes place. The setting of the oscillatory stop position can be performed in a manner substantially identical to that of the start-stop position and in fact the two positions can be identical. Preferably, in operation, the controller allows rotation of the motor in one direction for a fixed length of time before reversing direction when, after the allowed time expires, the driven surgical member reaches the predetermined or selected oscillatory stop position.

In this manner, the surgical device can be controlled so that it always starts, and/or reverses, at a known position at which an aperture at a distal end of the surgical device has a known open, closed, or partially opened characteristic.

The invention provides, advantageously, repetitive and precise operation of the surgical cutting device which promotes both efficiency and reliability for the system when the controller is used, for example, in arthroscopic surgery for the cutting and removal of tissue and other material.

The surgical control system has particular application for drawing tissue into a motor driven surgical cutting blade for resectioning and/or for fluid control.

The novel features which are considered a characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PARTICULAR EMBODIMENTS

Figure 1:
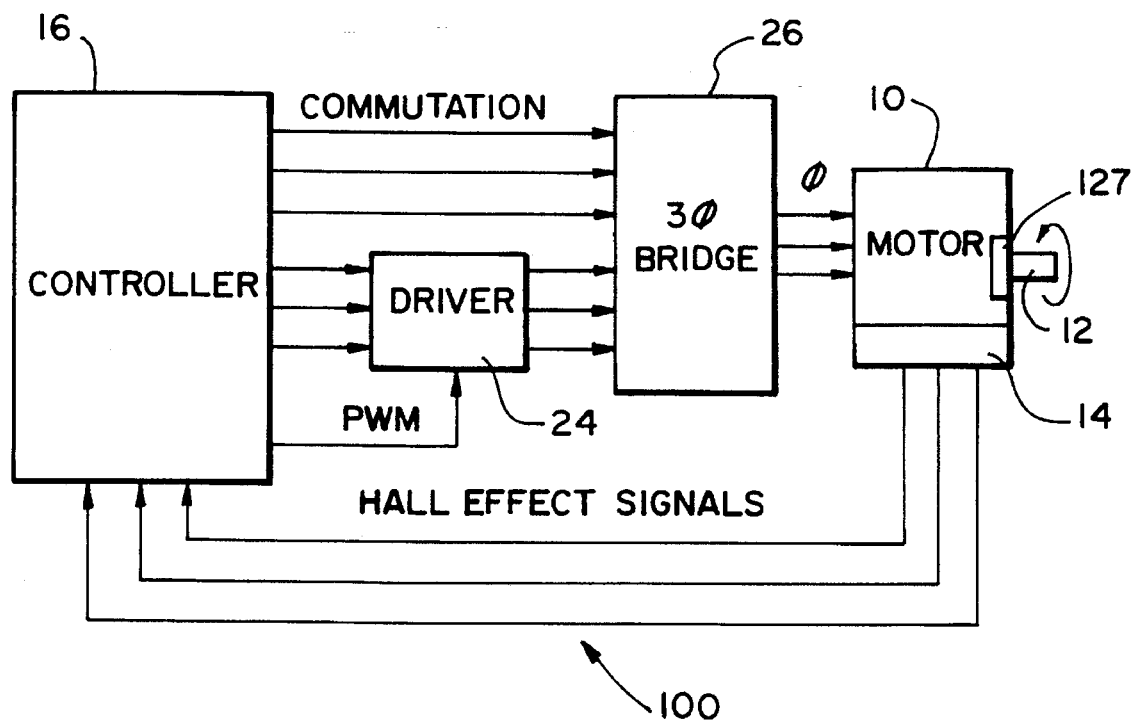
FIG. 1 is a general block diagram of the overall all-digital speed and position control system according to the invention.

The present invention is illustrated in terms of a control system for controlling the speed and more particularly for purposes of this disclosed invention, the relative position, of a motor, here a brushless three-phase, DC motor. Referring now to FIG. 1 the all-digital motor control system of this invention has a brushless, three-phase, DC motor 10 having a rotating armature 12. The motor has a plurality of conventional Hall effect sensors 14 mounted about the armature to sense armature position.

Figure 2:
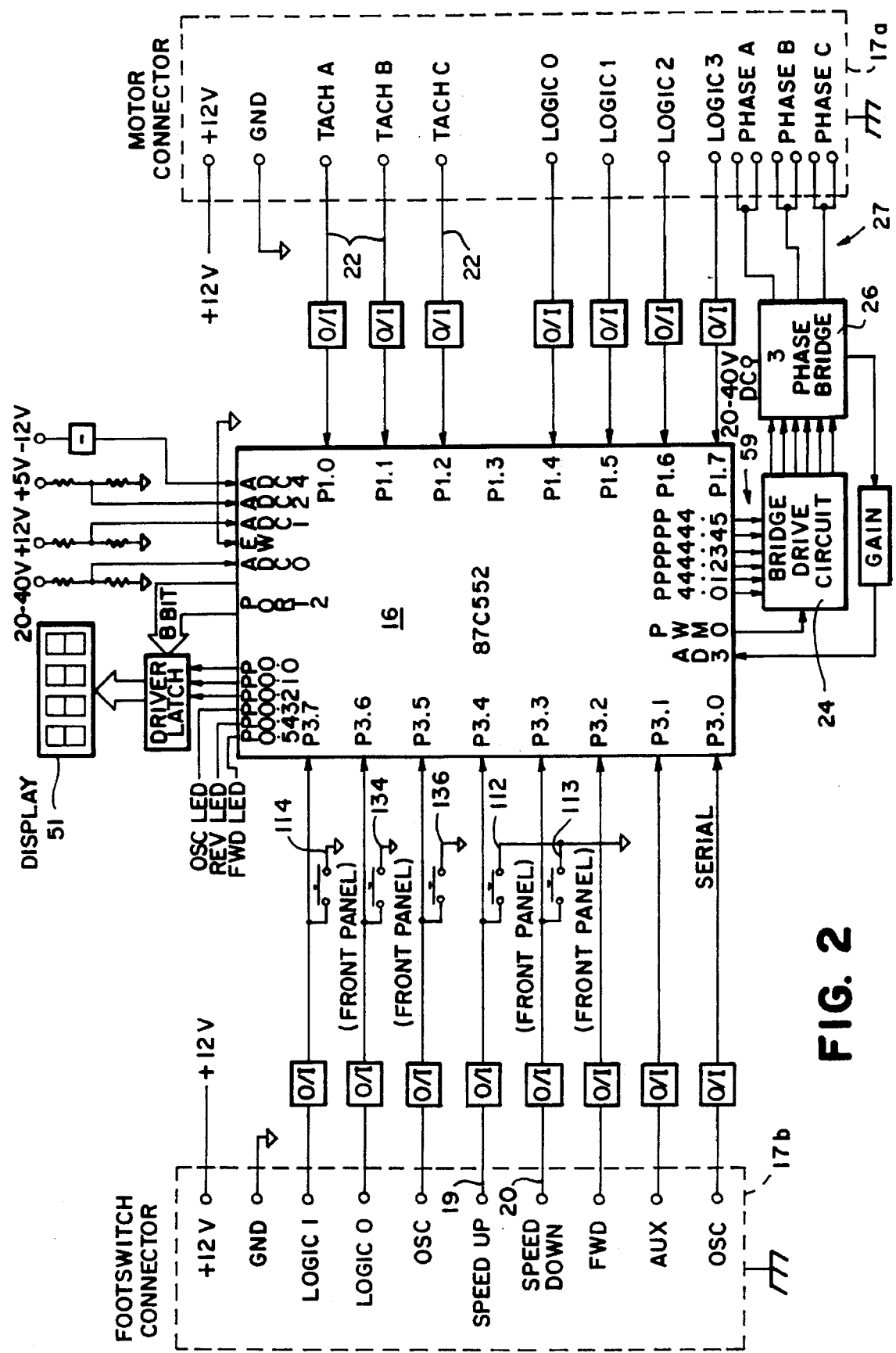
FIG. 2 is a detailed block diagram of a particular embodiment of the system of FIG. 1.

The system includes a digital signal processor or controller 16, preferably constituted as integrated circuit chip manufactured by Philips as No. 87C552. Controller 16 connects to motor 10 and a foot pedal switch (not shown) through connectors 17a and 17b respectively. Controller 16 generates an internal digital speed signal indicative of a desired armature speed based on the speed-up and speed-down signals over lines 19 and 20 (FIG. 2). The processor (or controller) 16, as will be described in detail below, also determines a motor output speed indicative of the actual armature speed from signals over lines 22 from the Hall effect devices.

Upon power turn-on, controller 16 executes a software program as set forth, in pertinent detail, on pages A-1 through A-8 of the attached Appendix A. Controller 16 generates a set of six commutation signals, two for each phase of the illustrated four pole brushless motor, together operative for rotating the armature. More specifically, the controller in the illustrated embodiment, includes in its program, a look-up table having a listing of six commutation bit patterns, each pattern representing a discrete command for the armature, as a function of the angular position of the armature, as determined by the signals from the Hall effect devices. The commutation signals are fed through, and processed in, a three-phase bridge circuit 26, and optionally, through a bridge driver circuit 24 (see FIG. 2), whereby three position control signals, one for each phase of the motor drive, are output to the motor 10 over lines 27. (The Hall effect sensors 14 sense rotation of the armature and generate two-state Hall effect signals, in response to which the controller 16 generates the commutation signals.)

Figure 3:
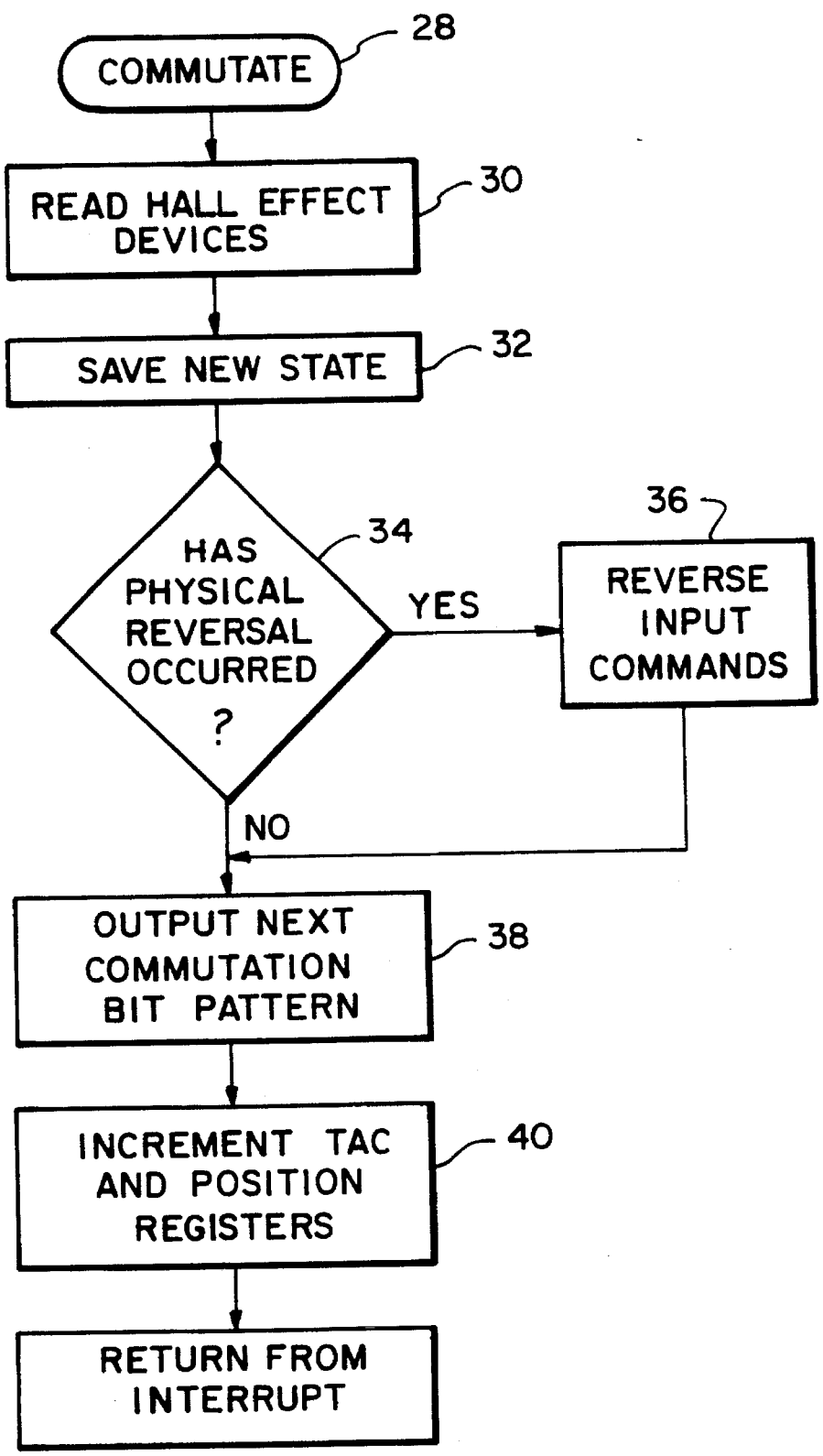
FIG. 3 is flow chart depicting part of the operation of the controller.

This latter aspect of the controller 16 is illustrated in the operations flow chart of FIG. 3. The generation of the commutation signals is indicated by block 28. The reading of the Hall effect sensors is denoted by block 30. The new state is stored at 32. When the controller 16 recognizes that a physical reversal of the armature has occurred (block 34), the reverse input command is given (block 36) and the next commutation bit pattern is output to the motor (block 38). If no reversal has occurred, the commutation bit pattern is sent without passing through block 36. Thereafter, an internal counter, operative for generating a tachometer (TAC) signal, and the position registers, as described hereinafter, are incremented (block 40). The controller then returns from the interrupt. (For the illustrated four pole (3 phase) motor, the bit pattern changes every 30° of armature mechanical rotation.) The tachometer signal is processed to generate the aforementioned speed signal.

Figure 4:
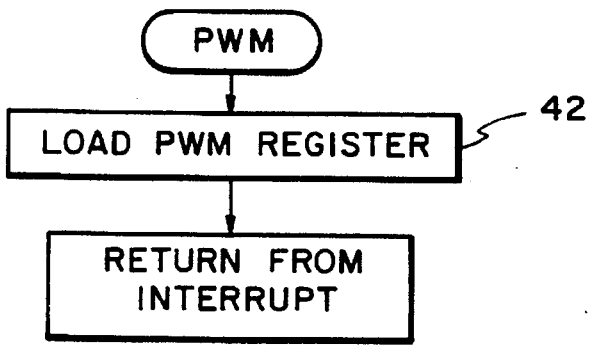
FIG. 4 is a flow chart depicting another aspect of the operation of the controller.

Referring to FIG. 4, controller 16 also generates, by loading a PWM register in response to the desired speed value, a digital pulse width modulated (PWM) signal having a duty cycle (or pulse width) dependent upon armature rotational velocity. (Block 42) The PWM signal, in the illustrated embodiment, has a fixed PWM cycle of 42.5 microseconds. The PWM signal has a high and a low state. The controller determines the duration of the PWM signal and hence the speed of the armature in the preferred case, from 0 –42.5 μs. In this way, the duty cycle of the PWM signal is controlled from 0–100%.

As shown in FIGS. 1 and 2, the PWM signal is fed to a bridge drive circuitry 24 which generates switching signals for the three phase bridge 26 as is well known in the art. In turn, the bridge 26 generates, for each phase, the aforementioned motor control signals. each having an on-state and an off-state.

The Hall effect sensors, as previously mentioned, generate and send relative position signals back to the controller where the signal changes are accumulated as they occur. The resulting counts from a TAC counter are processed by controller 16 to generate a tachometer signal which is delivered by the processor 16 to a display 51 and is indicative of the actual rotational speed of the motor.

Figure 6:
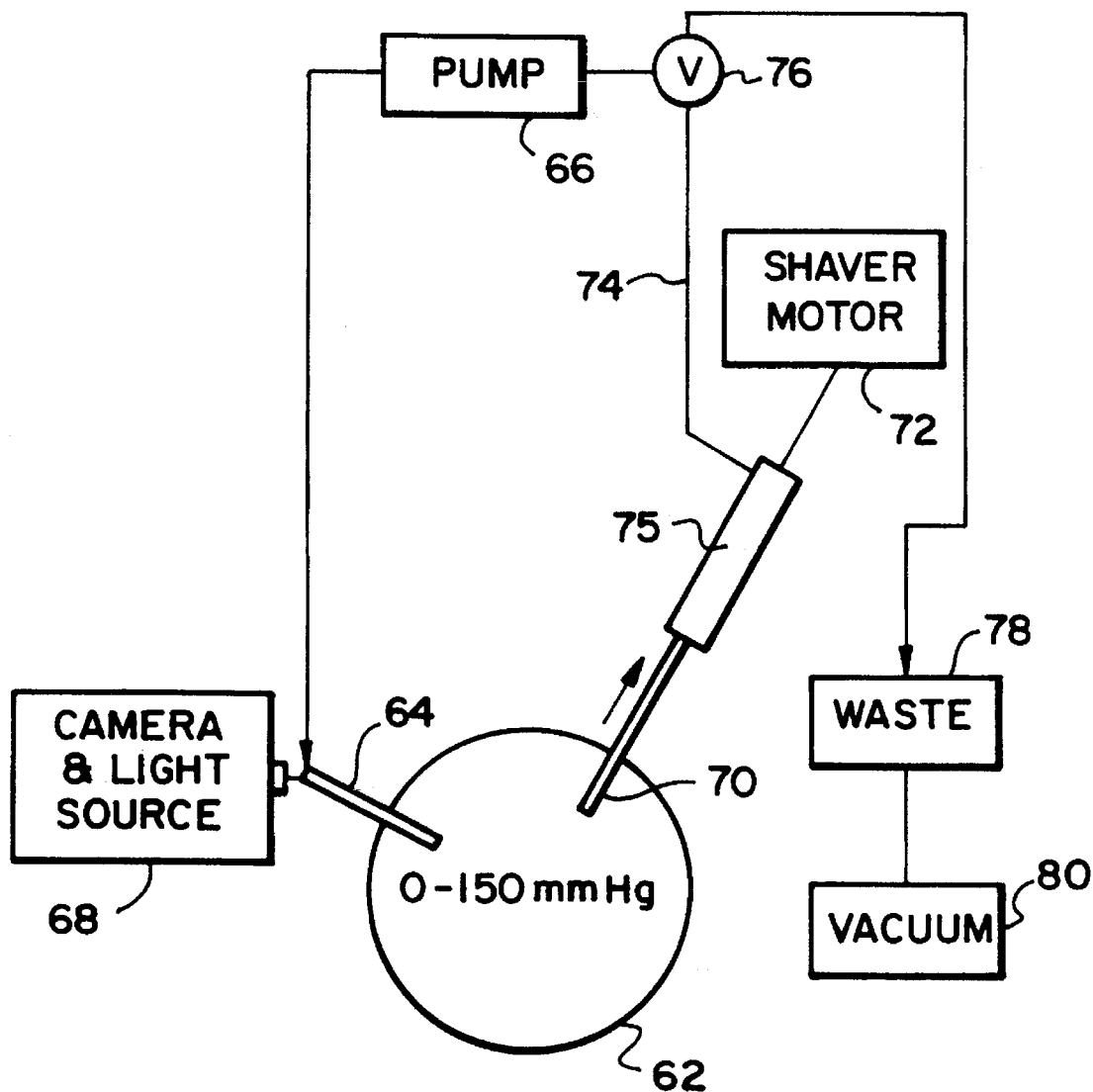
FIG. 6 is a schematic block diagram of a surgical procedure, using the system of the invention.

FIG. 6 is a schematic block diagram showing a setup of a typical modern surgical procedure, for example, an arthroscopy or laparoscopy. A joint or another area of the patient being operated on is shown at 62. A first cannula 64 is introduced into the area and is attached to a source of saline solution. A pump 66 maintains a positive pressure in the joint, for example 0 to 150 mm Hg gage. A video camera and light source 68 are also connected to the cannula 64 for viewing the area and displaying the image on a television monitor (not shown). A second cannula 70 with a surgical instrument at its end is also introduced into the area 62. The instrument, here, is a hand-held shaver with a motor drive 72. The saline, blood and debris from the cutting are removed from the area through a hollow in the cannula 70 and then through a hose 74 which passes to a pinch valve 76, located on the pump housing 66, and which can help regulate flow from the area. The effluent then passes to a waste collector 78 and to a vacuum source 80 which typically maintains a pressure of 150 to 760 mm Hg absolute. Between the cannula 70 and hose 74 is the remainder 75 of a surgical device.

It is important in such procedures that the pressure in the area 62 remain constant. This is particularly difficult to maintain in the area of a joint where the mechanical dimensions of the joint are constantly changing, and the joint is leaking and represents an unstable and unsealed volume. As the surgeon operates the surgical system, opening and closing the connection to the vacuum and removing bits of tissue with the fluid flow, there can be a quickly changing vacuum. It is essential for good surgical procedures that the pressure in the surgical area be constant. Particularly important is that the pressure never become too large, as this would injure the patient. Constant pressure is directly related to accurate control over the velocity of the saline flowing into the area 62. Small changes of pump speed yield very large changes in pressure. It has been found that with the control system of the present invention, a substantially constant pressure, to very tight tolerances, can be maintained. This is particularly achieved with a pulse driven motor in the pump, where the drive pulse duty cycle can be varied, and accordingly where the frequency of revolution can also be varied from a fraction of an RPM to, for example, 1000 RPM. Typical flow rates into a surgical area are from 0.0 to 2.5 liters per minute.

Figure 7:
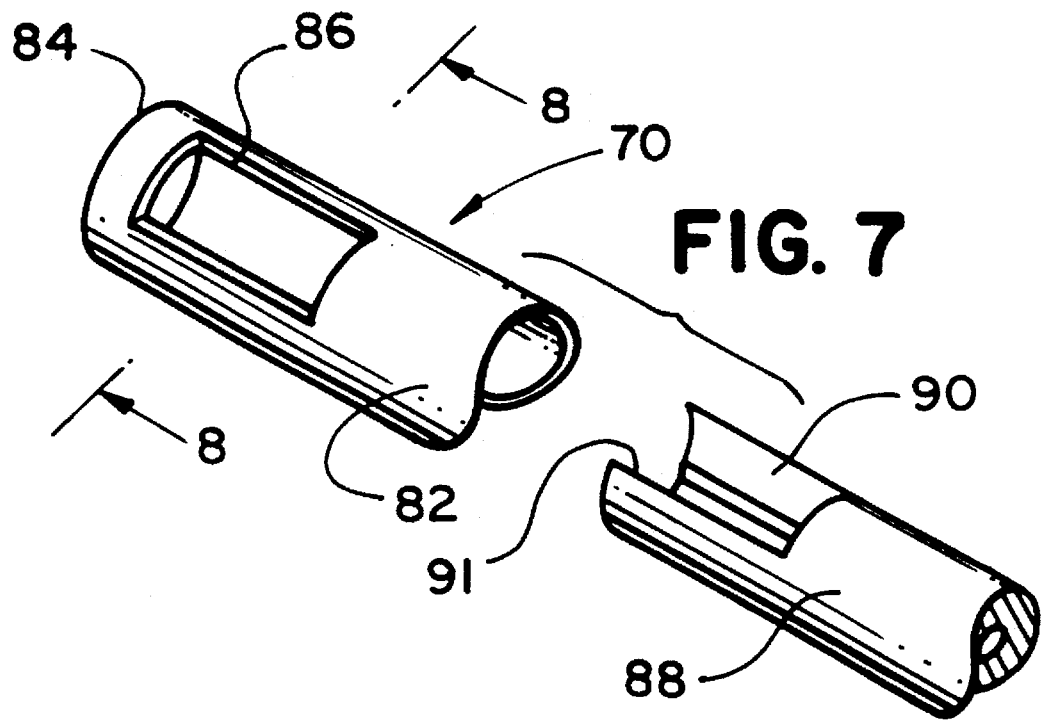
FIG. 7 is a perspective view of a surgical tool.

FIG. 7 is a schematic perspective, partially cut away, exploded view of part of a surgical device, a blade assembly, which would appear at the end of the cannula 70. A fixed hollow tube 82 of the blade assembly, closed at its distal end 84, has an opening which describes typically a cut-out section 86. The rotatable inner blade 88, also a hollow tube, has a cutting surface with sharp edges 91 at its distal end region 90. The inner blade is driven by the motor and rotates inside the tube 82 which is securely housed in the motor assembly. The vacuum draws fluids and debris through the central hollow for removal.

The inner blade is typically driven at a constant speed, and rotates either in a continuous, single direction, mode, or in an oscillatory mode. The inner blade is driven by the motor within the shaver 72 corresponding to motor 10. It is desirable to control accurately the torque applied to the inner blade, because if the torque is too large, for example due to a piece of bone or metal or other fragment getting caught in the spinning tube of the inner blade 88, the inner blade itself or the tube 82, or the cannula 70 may shatter with the result of spraying debris into the patient's joint. The debris, then, must be removed which is not an easy task. Also, there is the resulting attendant trauma to the region. The control system of the present invention provides such a torque control.

As noted above, the system of the present invention applies a voltage or electrical drive energy, for example, a series of pulses with a particular duty cycle, to the brushless motor. The tachometer measures the actual speed of the motor armature, as noted above, and compares the desired armature rotational speed with the actual output speed derived from the Hall effect sensor waveforms (FIG. 10) from the driven motor. If an object becomes stuck inside the surgical device, the motor will normally need more power, and thus will call for an increased duty cycle in the form of more average voltage and/or current. The software compares the actual speed of the motor with the commanded speed of the motor, and if the speed is too slow for the applied voltage, then the controller will decrease the duty cycle, (which correspondingly reduces the average voltage or current), and this will cut down on the torque, and thus will avoid possible fracture of the inner blade 88 or the tube 82. The surgeon may then observe the condition at the end of the cannula through the camera 68; and if something is stuck, increase the flow of saline or manipulate the tool to remove the clogging. It is also desirable in this situation to stop the tool with the aperture open. As will be described below, the invention allows this condition to be attained if originally preset into the system. If need be, also, the surgeon can change the tool.

Figure 8:
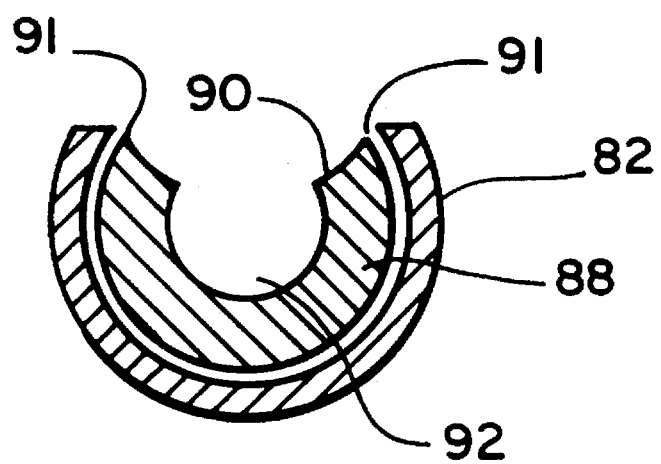
FIG. 8 is a cross-sectional view through FIG. 7.

FIG. 8 is a cross-sectional view through the cannula of FIG. 7 but with the inner blade inserted therein. The inner blade 82 with its cutting edge 91, in the present invention, may be driven to rotate one way, and then another, that is, to oscillate. For example, the system can drive the inner blade clockwise for 0.6 seconds, then counter-clockwise for 0.6 seconds, and thereafter repeat that process. As the inner blade body 88 rotates one way and then the other, tissue that moves into the opening 86 is cut, and is then removed by the action of the vacuum, by flushing the saline solution through the interior hollow aperture 92, which feeds ultimately to the hose 74.

It is understood that the oscillatory movement is not limited to rotary inner blades, but may be used for drills, circular rasps, rotary rotating scalpels, and a full range of motor driven tools.

It is also desirable, in accordance with the invention, as noted above, that the inner blade 88 start, and stop, in either mode of operation, a continuous mode of operation or an oscillating mode of operation at a known position. In the continuous mode, the inner blade begins operation in one direction and terminates operation under control of the user, but does not reverse. In this mode, it is desirable that the inner blade start and stop at the same location, for example when its aperture and cutting edges are aligned, that is, substantially, with the aperture in the distal end of tube 82, at cutout section 86. Thus, control upon starting and stopping of the inner blade is desirably achieved, and thereby the aperture may be left open, allowing vacuum and the resulting flow of solution to continually clear the area of the surgical event, or, on the other hand, may be left closed or only partially open when those positions are determined to be desirable. Similarly, the ability to start the operation of the surgical device, at the same location each time, gives the surgeon the ability to predict with substantial certainty the type, location, and quantity of tissue to be resected.

It is also advantageous, and particularly useful for the surgeon, in the oscillatory mode of operation described above, that the reversal of direction always takes place with the aperture in the same condition, that is, preferably open, possibly closed, or at some position therebetween. This provides therefore that, for example, no effluent shall be withdrawn from the joint during the reversal process, or on the other hand that some or a full flow of effluent will be withdrawn from the joint during reversal, at a time when tissue cannot be cut since rotational motion will have stopped, if only momentarily. The ability to predict with certainty that the reversal will take place in a known and predictable manner provides substantial advantage to the described surgical device. In accordance with the invention, the controller is capable of effecting aperture control, as described above, in the following manner.

Figure 9:
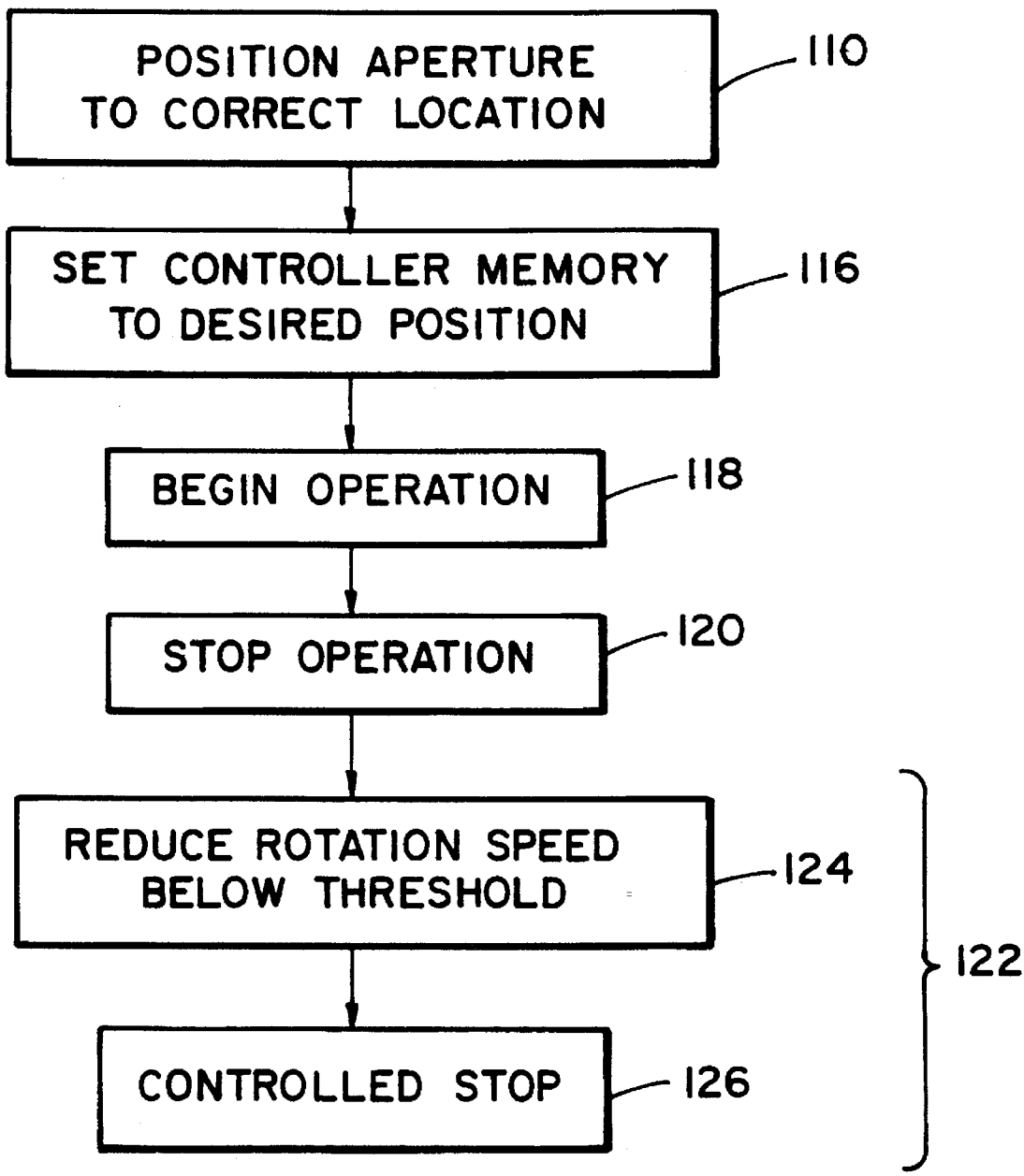
FIG. 9 is a flow chart of another aspect of controller operation according to the invention.

Referring now to both FIG. 2, the flow chart of FIG. 9, and the software Appendix, in a preferred embodiment of the invention, the controller 16 operates in an open loop fashion. That is, the controller learns a position from which desired start and stop operations are to be effected, and tracks the position of the driven portion of the surgical device from that location, based upon the Hall effect signals coming from the drive motor over lines 22 and the knowledge, built into the programming of the controller, of the nature of the motor and any gear reduction mechanism interconnected between the motor armature shaft and its eventual output shaft 12. In the illustrated embodiment of the invention, the motor is a four pole (three phase motor) having a 5:1 gear reduction mechanism which thus requires five turns of the armature of motor 10 for each single turn of the output shaft 12.

Upon initial operation, the user, or surgeon, increments the surgical device to position its aperture at its distal end to its correct location (block 110). This can be accomplished effectively by providing a speed up switch 112 which, upon actuation, causes the motor to slowly increment and hence to move the driver inner blade, in one illustrated embodiment, until it properly aligns itself with the opening in tube 82. This can be, as noted above, to provide either an open, closed, or partially open aperture. In the particular embodiment of the invention, switch 112 is complemented by switch 113 so that the motor can increment in either the forward or reverse direction. Once the motor has been set to the desired position, a third switch 114 is actuated to set the controller memory to that position (block 116). This results in clearing a memory counter of controller 16 which is then incremented each time there is a change of state on any of Hall effect switch lines 102, 104, 106.

In the preferred embodiment of the invention described in the software of Appendix A, the switches 112 and 113 (or their foot pedal equivalents, if any) are simultaneously depressed. In response, the controller increments the driver inner blade and, upon release of the switches at a desired position, the controller resets the memory counter to "zero" corresponding to the desired start-stop position.

Figure 10:
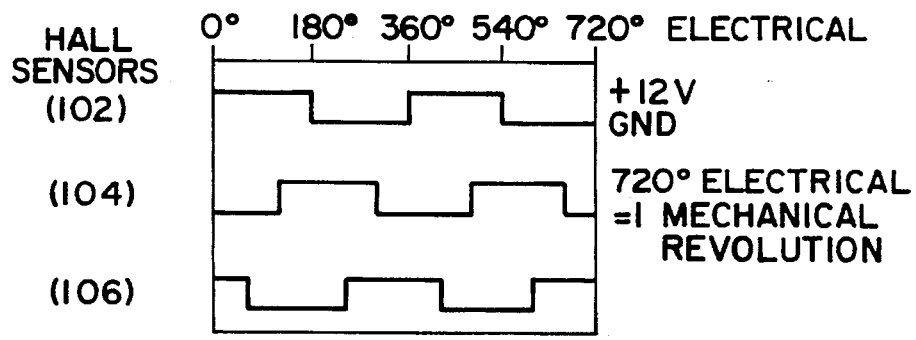
FIG. 10 depicts the Hall effect switch outputs according to the invention.

Referring to FIG. 10, it will be seen from a review of the signals coming from the Hall effect switches that 12 changes of state occur for each 720 degrees of the electrical cycle, corresponding to one complete revolution of the armature. Accordingly, for one complete revolution of the output shaft 12 there are 60 changes of state provided by the motor sensors over lines 22. In the controller, therefore, a counter is provided which counts forward or backward, depending upon the direction of motor rotation, modulo 60, and the controller software recognizes that once set, the motor must stop at a location corresponding to a count of "zero". Thus, after the controller memory is set (to "zero") at 116, continuous or oscillatory operation can be initiated, at 118. During the continuous mode of operation, the motor operates in a first direction (forward or reverse) and continues to do so, in accordance with the description here and above, until a stop command is given.

In the preferred embodiment of the invention, the operation of the motor is initiated by depressing a foot pedal (not shown) and the release of the foot pedal acts as a stop switch to command the controller to terminate rotation of the motor 10. This is indicated at 120. The controller, however after recognizing the actuation of the stop command, continues to rotate the motor so that it will stop at the previously predetermined condition, in this embodiment corresponding to a count of zero in its counter. This is indicated at 122. However, as noted at block 124 if the rotational speed of the motor is greater than a defined threshold, the motor first is slowed down to a speed below that threshold value (for example 1,000 rpm) in accordance with a preferred embodiment of the invention and is then brought to a controlled stop, at the predetermined position, at 126. This occurs, in particular, with brushless motors since, unlike, for example, stepping motors, the motor is built so that the inertia of the motor drive helps to carry the armature forward from position to position.

In the illustrated embodiment of the invention, the control loop operates as an asynchronous, position error, control loop. This method of control is generally simple to implement, however, other methods including synchronous control and/or a velocity error control loop may also be employed, and in certain circumstances may provide improved accuracy in stopping at the start-stop position.

The accuracy with which motor armature position is known is determined by the frequency with which state changes occur over lines 22, and, since 60 state changes occur for each full revolution of the output shaft in this illustrated embodiment (taking into account the 5:1 gear reduction ratio of reducer 127 of the motor), it can be determined that a change of state over lines 22 occurs every 6 degrees of surgical device rotation. (See also FIG. 10) Thus, the accuracy of stopping of the motor is approximately plus or minus 6° (360° of rotation divided by 60) ignoring other errors.

In this open loop control mode, it is also important that the gear reduction ratio have a value "a" that must be an exact multiple of 1[number of Hall effect state changes per armature revolution] (1/12 in the illustrated embodiment). Otherwise, the position of the driven member may "creep", thus resulting in errors in positioning the surgical device driven member both at the start-stop position, and at the reversal position described below.

Figure 5:
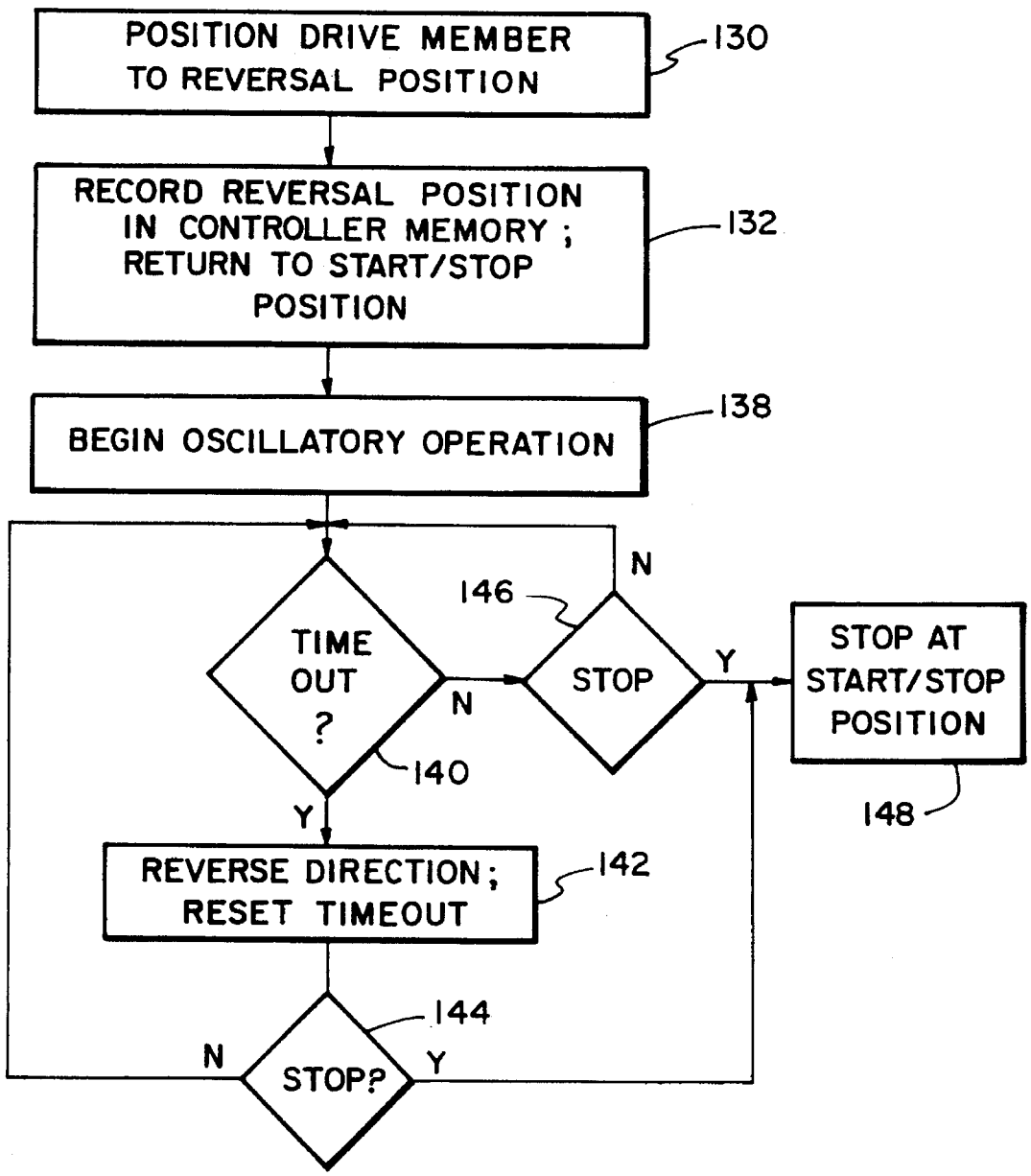
FIG. 5 is a flow chart depicting still another aspect of the controller operation according to the invention.

In the preferred embodiment of the invention, referring now to FIG. 5, and as noted above, the motor and controller can advantageously operate in an oscillatory mode. In this mode, in a preferred embodiment of the invention, the user has the ability to set a second position, an oscillatory mode reversal position at which the reversal of the motor takes place. Referring to FIG. 5, the operator or surgeon first positions the driven member of the surgical device so that, for example, the driven member is at the correct opening location at which the surgeon desires reversal to take place. This is indicated at block 130. Once that position is set, (using switch 112 as before), the controller memory is set to record that position. Note that here, the reversal position is set after the start-stop position has been set and accordingly, typically, the position will be at a location other than the start-stop position. A separate tracking counter can be used by the controller for tracking armature position relative to the reversal position. Alternatively the start-stop tracking counter can be used. (The default value for the reversal position is the start-stop position). That value is recorded by the controller and once recorded the surgical device is returned to the precorded start-stop position. This is indicated at block 132. A separate switch 134 can be used to record the oscillatory mode reversal position. However, in accordance with the preferred software of Appendix A, once the controller is in the oscillatory mode of operation, the procedure noted above of simultaneously closing and then releasing switches 112 and 113 can be used to move the driver inner blade to a desired position and storing the position in an oscillatory tracking counter when the switches are released.

Oscillatory mode operation can then be effected by actuating a switch 136. Upon actuating switch 136, the motor begins to move in a first direction and will continue to do so for a fixed length of time, in the illustrated embodiment. In other embodiments, the number of revolutions can be set, however, in the preferred embodiment, it is considered better to use a fixed length of time, for example less than 1 second, and preferably about 0.6 seconds. Once oscillatory operation begins, as noted at block 138, the direction of movement of the surgical device continues in the same direction until time out of the time period has occurred. This is indicated at 140. After the time out occurs, the controller continues the direction of motor rotation until it reaches the oscillatory reversal position at which location the controller effects a reversal of direction. This is indicated at 142. The time out timer is then reset, for example to 0.6 seconds, and the system recycles unless a stop command had been given as indicated at 144. If, during the time when the time out counter is running, a stop command is given as noted at 146, the system escapes from the time out loop to terminate rotation at the next traversal of the start-stop position (unless rotation velocity exceeds threshold as noted above). This is indicated at 148.

At any time during the surgical procedure, if a new surgical device is introduced into the motor, or if the physician desires to reset either the start-stop or oscillatory reversal positions, the procedures noted above in connection with FIGS. 5 and 9 need to be repeated. Thereafter, operation of the system proceeds as described hereinabove.

In accordance with the preferred embodiment of the invention, there has been described an open loop system. It is possible that in the open loop configuration the relative position of oscillatory reversal or start-stop positions may vary due to decoupling of the tracking mechanism with the armature physical position due to extraneous influences. It is therefore possible, should further security be desired, or for other reasons, to operate the system in a closed loop configuration by adding addition magnets and/or sensing elements to the handpiece and/or the surgical device.

Figure 11:
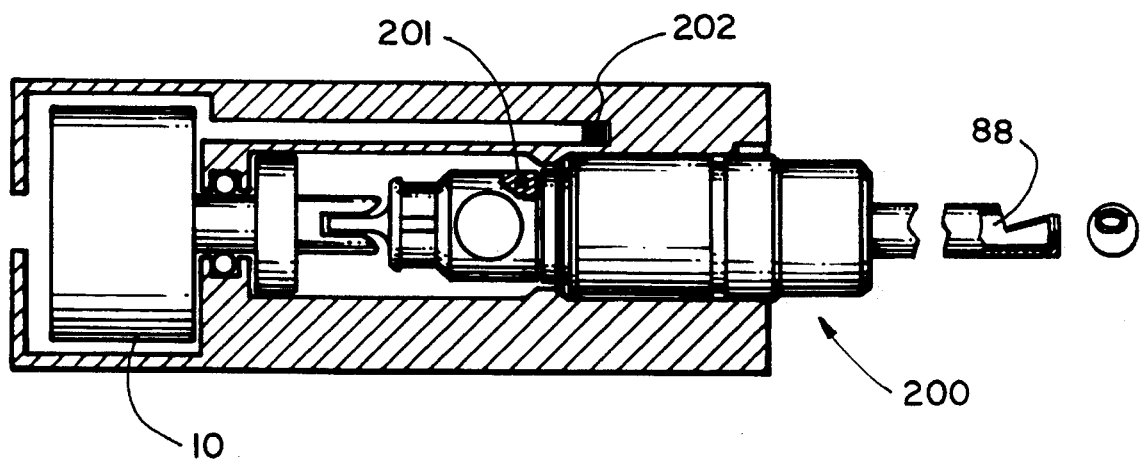
FIG. 11–13 are schematic diagrams of different embodiments of the closed loop method of operation.

Referring now to FIG. 11, there is illustrated a motor 10 connected to a surgical device 200 and wherein a magnet 201 is embedded in the outer circumference of the proximal end of the rotating driven surgical member, here inner blade 88. A Hall effect receiving element 202 is embedded within the motor handpiece to establish an absolute reference point for the surgical system. Thus, the controller, which can receive an electrical signal from the Hall effect receiving switch 202, can determine with precision when the inner blade is positioned opposite the Hall effect receiving switch 202. In this embodiment, in accordance with the preferred use of the closed loop method, the controller uses the signal from Hall effect switch receiving element 202 to supplement and check the signals which are derived as noted above in connection with the open loop process. There are two reasons for this. First, the physician may not want to use, as either the start/stop position or the reversal position, the aperture setting corresponding to the alignment of the magnet 200 in the proximal end of the inner blade with the Hall effect switch receiver 202. (In fact, unless the devices are one-way keyed, this is a random alignment.) Second, because only one magnet is provided in this embodiment, and because it is impossible to stop the brushless motor of the current design "on a dime" the actual end stopping point may not only be variable, but will be other than that designated by the magnet; and in fact, the end point will be a function of the rotational speed of the motor at the time the magnet passes by receiver 202.

The closed loop method can be used to provide the additional control described above in addition to the open loop method.

Figure 12:
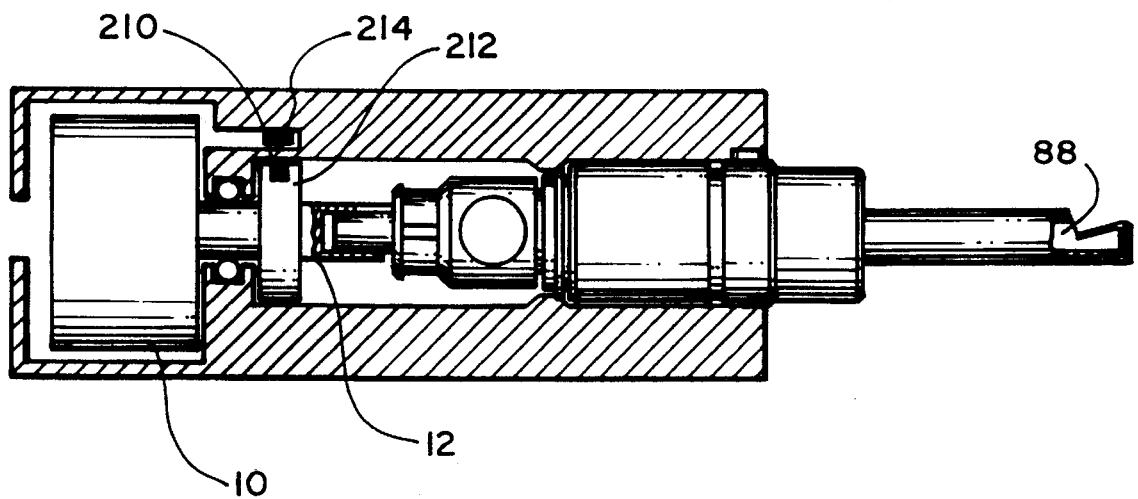

Referring to FIG. 12, in a second embodiment of the closed loop method, a rotating magnet 210 is embedded in moving motor drive shaft 12, at 212. A corresponding Hall effect receiving switch 214 is positioned within the motor handpiece to establish a precise reference point for motor control; however, in this embodiment, the drive shaft into which the surgical device is received must have a single orientation with regard to the driven member in order to properly define the member (aperture) with respect to the drive shaft magnet 210. This embodiment suffers the same resolution issues described above in connection with the embodiment of FIG. 11.

Figure 13:
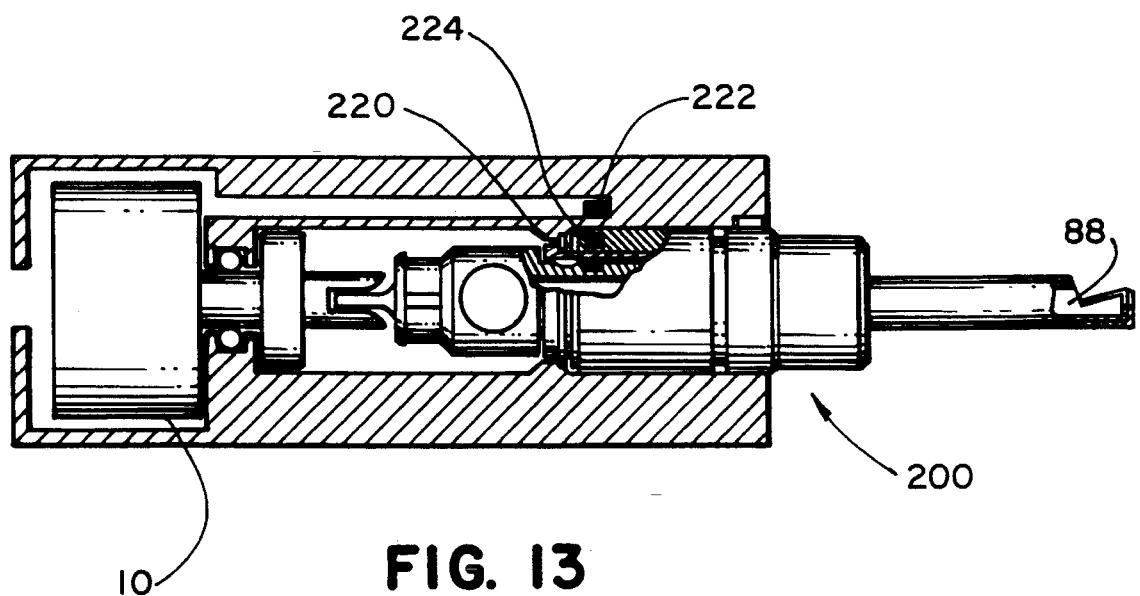

Referring now to FIG. 13, in yet a third embodiment of the closed loop method, a single modulating element, a magnet 220 embedded in the rotating portion of the inner driven member of the surgical device, and aligned with existing receiving Hall effect switches 222 and with already existing device type sensing magnets 224 can provide another method for the controller to determine absolute positioning of the driven rotating member relative to the fixed tube member 82. However, as with the embodiments illustrated in connection with FIGS. 11 and 12, this embodiment also suffers from the same resolution problems which can be resolved by either closed loop or open loop techniques.

Other embodiments of the invention for controlling the stop and start position as well as the oscillatory reversal position of a driven member of a surgical device relative to the fixed member of the same device will be apparent to those practiced in the art. They might include, for example, designing complex algorithms associated with the closed loop approaches, the use of more accurate stepper motors as opposed to the brushless motor preferred and described herein, and other methods for increasing resolution of the system such as an optical encoder. These, and other embodiments of the invention will be apparent to those practiced in these arts that are within the scope of the following claims.

While the invention has been illustrated and described as embodied in an all-digital speed control system for a brushless three-phase DC motor, it is not intended to be limited to the details shown, since various modifications and structural changes may be made without departing in any way from the spirit of the present invention.

APPENDIX A                                                                       A-1

```
state            mov      sp,#stack              ; reset stack
                 mov      r7,a                   ; save new
                 mov      b,#0                   ; 256 consecutive reads
state0           acall    status
                 djnz     b,stat0
                 jnb      lock.2,stat1           ; test for jog mode
                 mov      posit,#0
                 mov      pwm0,#0
                 clr      lock.2
                 orl      iex1,#7                ; enable ct interrupts
stat1            mov      dptr,#st_table         ; goto new state
                 jmp      @a+dptr
st_table                                         ; UDFR
                 ajmp     state0                 ; 0000 display set
                 ajmp     state1                 ; 0001 run reverse & display rpm
                 ajmp     state2                 ; 0010 run forward & display rpm
                 ajmp     state3                 ; 0011 oscillate & display rate
                 ajmp     state4                 ; 0100 decrement and display set
                 ajmp     state4                 ; 0101
                 ajmp     state4                 ; 0110
                 ajmp     state7                 ; 0111 decrement oscillate rate
                 ajmp     state8                 ; 1000 increment and display set
                 ajmp     state8                 ; 1001
                 ajmp     state8                 ; 1010
                 ajmp     stateB                 ; 1011 increment oscillate rate
                 ajmp     stateC                 ; 1100 jog & lock on armature position
                 ajmp     stateC                 ; 1101
                 ajmp     stateC                 ; 1110
                 ajmp     stateC                 ; 1111
status
                 acall    device
                 mov      a,timeout
                 jnz      s0                     ; check serial port timer
                 mov      stat,a                 ; force serial data to 0
                 mov      a,p3
                 cpl      a
                 mov      c,acc.1
                 orl      c,acc.2
                 jnc      s3                     ; check for forward or reverse
                 mov      target,#-1             ; turn on full speed
                 sjmp     s1
s3               mov      target,#0              ; turn off
s1               jnb      acc.5,s2
                 orl      a,#6                   ; set oscillate function
s2               anl      a,#1Eh
                 cjne     a,7,state
                 ret
s0               mov      a,p3                   ; serial input
                 cpl      a
                 anl      a,#18h                 ; buttons
                 rr       a
                 orl      a,stat                 ; combine with serial stat
                 rl       a
                 sjmp     s2
run
                 mov      r0,dsr
                 mov      set,@r0
                 acall    rpmdsp
                 mov      tic,mpb+11             ; 1 second display hold
```

A-2

```
run0        acall       status
            mov         a,tic
            jnz         run0
            mov         r4,tac
            mov         r5,tac+1
            acall       format
            acall       display             ; display rpm actual
            mov         tic,mpb+13          ; 1/2 second update rate
            sjmp        run0
state0                                      ; DISPLAY SET
            setb        lock.3
            mov         p0,#11000100b       ; turn off LEDs
            mov         r0,dsr
            acall       rpmdsp              ; display set
st00        acall       status              ; wait for change
            sjmp        st00
state1                                      ; RUN REVERSE
            mov         lock,#0
            mov         dir,#28h
            mov         p0,#11010100b       ; reverse LED
            ajmp        run
state2                                      ; RUN FORWARD
            mov         lock,#0
            mov         dir,#20h
            mov         p0,#11100100b       ; forward LED
            ajmp        run
state3                                      ; OSCILLATE & DISPLAY RATE
            acall       oscdsp              ; display oscillate message
            mov         tic,lag
st31        acall       status
            cir         p0.5                ; strobe pulse
            mov         a,target
            jnz         st32
            mov         p0,#11000100b       ; turn off LEDs
            sjmp        st31
st32        mov         p0,#11001100b       ; oscillate LED
            mov         a,tic
            jnz         st31
            setb        lock.0              ; tell velocity to change direction
            mov         tic,mpb+14          ; oscillate period .6 seconds
            sjmp        st31
state4                                      ; SLOW DOWN
            mov         tic,mpb+11          ; 1 second
st40        mov         r0,dsr
            mov         a,@r0
            cir         c
            subb        a,mpb+4             ; clamp at min
            cjne        a,mpb+5,$+3
            jc          st42
            mov         @r0,a               ; save new
st42        mov         set,@r0
            acall       rpmdsp              ; display set
st41        acall       status
            mov         a,tic
            jnz         st41
            mov         tic,mpb+15          ; 40 msec slew
            sjmp        st40
state7                                      ; DECREASE RATE
            mov         tic,mpb+11          ; 1 second hold
st71        mov         a,index
```

A-3

```
              jz        st72
              dec       index
st72          acall     oscdsp
st70          acall     status
              mov       a,tic
              jnz       st70
              mov       tic,mpb+16           ; .24 sec slew
              sjmp      st71
state8                                       ; SPEED UP
              mov       tic,mpb+11           ; 1 second
st80          mov       r0,dsr
              mov       a,@r0
              add       a,mpb+4
              jc        st82
              cjne      a,mpb+6,$+3
              jnc       st82                 ; clamp at max
              mov       @r0,a                ; save new
st82          mov       set,@r0
              acall     rpmdsp               ; display set
st81          acall     status
              mov       a,tic
              jnz       st81
              mov       tic,mpb+15           ; 40 msec slew
              sjmp      st80
stateB                                       ; INCREASE RATE
              mov       tic,mpb+11           ; 1 second hold
stB2          mov       a,index
              cjne      a,#9,stB0
              ajmp      stB3
stB0          inc       index
stB3          acall     oscdsp
stB1          acall     status
              mov       a,tic
              jnz       stB1
              mov       tic,mpb+16           ; .24 sec slew
              ajmp      stB2
stateC                                       ; JOG
              anl       iex1,#0F8h           ; disable ct interrupts
              mov       pwm0,#25
              setb      lock.2               ; tell velocity to run synchronously
              mov       dptr,#mag1
              acall     message              ; display message
              acall     display
stC0          acall     status
              sjmp      stC0

; VELOCITY handles burshless motor velocity vector requirements
; KK930712
;   R0:  int_buf pointer
;   R1:  dtac
;   R2R3: proportional error
;   R4R5: integral error
;   R6:  floating target velocity for loop jog           acall     commutate            ; run synchronously
              ret
velocity                                     ; timer 0 reset before vectoring here
              jb        lock.2,jog
              push      acc
              push      psw
```

A-4

```
              push     b
              setb     rs1                    ; use register bank 2 mov      a,tic                  ; general purpose timer for other
              jz       swi                    ; routines
              dec      tic
              clr      a
swi
              clr      c                      ; sliding window integrator
              xch      a,dtac                 ; get and reset (no interrupt trouble)
              mov      r1,a                   ; save for velocity loop
              xch      a,@r0                  ; get old and save new dtac in buffer
              xch      a,tac
              subb     a,tac
              mov      tac,a
              mov      a,tac+1
              subb     a,#0
              mov      tac+1,a                ; remove old value from swi
              mov      a,tac
              add      a,@r0
              mov      tac,a
              mov      a,tac+1
              addc     a,#0
              mov      tac+1,a                ; add new value to swi
              inc      r0
              mov      a,#int_buf
              add      a,mpb+10
              cjne     a,10h,direct           ; test buffer pointer for end
              mov      r0,#int_buf            ; reset pointer
direct
              jb       lock.0,wrong_way
              mov      a,target               ; velocity target from footswitch
              jz       v2
              mov      b,set                  ; maximum selected motor speed
              mul      ab
              inc      b                      ; scaled target velocity in b ; velocity profiler with direction control mov      a,r6                   ; velocity loop command compared to
              cjne     a,b,$+5                ; new target
              ajmp     v3
              jc       increase
              subb     a,mpb+7                ; decrease
              jc       v5
              cjne     a,b,$+3
              jc       v5                     ; IF carry clamp at b ELSE use new a
v2            mov      r6,a
              ajmp     v3
increase
              add      a,mpb+7
              jc       v5
              cjne     a,b,$+3
              jc       v2                     ; IF carry use new a ELSE clamp at b
v5            mov      r6,b
              ajmp     v3
wrong_way
              mov      a,r6
              cjne     a,mpb+8,$+3            ; reverse velocity
              jc       change
```

A-5

```
                clr     c
                subb    a,mpb+7
                jnc     v2
                mov     r6,#0
                ajmp    v3
change
                xrl     lock,#3              ; tell commutate to change direction
; velocity loop
v3              mov     a,r6                 ; calculate error
                jnz     v4
                mov     r4,a
                mov     r5,a                 ; reset integral term
                jnb     lock.3,ok2
                clr     lock.3
                setb    lock.1
                sjmp    ok2
v4              clr     c
                subb    a,r1                 ; subtract actual tac value
                mov     r2,a                 ; save proportional error
                clr     a
                subb    a,#0
                mov     r3,a                 ; save proportional error
                mov     a,r4                 ; low byte of integral term
                add     a,r2                 ; add low byte of proportional term
                mov     r4,a
                mov     a,r5                 ; high byte of integral term
                addc    a,r3                 ; add high byte of proportional term
                mov     r5,a
                clr     c
                mov     a,r1
                subb    a,r7
                mov     der,a
                mov     r7,11h
                clr     a
                subb    a,#0
                mov     der+1,a
                mov     a,r2
                add     a,r4
                mov     r2,a
                mov     a,r3
                addc    a,r5
                mov     r3,a
                mov     a,r2
                add     a,der
                mov     r2,a
                mov     a,r3
                addc    a,der+1
                mov     c,acc.7
                rrc     a
                mov     r3,a
                mov     a,r2
                rrc     a
                mov     r2,a
                mov     a,r3
                mov     c,acc.7
                rrc     a
                mov     r3,a
                mov     a,r2
```

A-6

```
            rrc     a
            mov     r2,a
            mov     a,r3
            jz      ok                      ; torque limit
            mov     r4,int
            mov     r5,int+1
            jnb     acc.7,too_big
            mov     r2,#0                   ; set at minimum
            sjmp    ok1
too_big     mov     r2,#0FFh                ; set at maximum ; torque limit ok          mov     a,r1                    ; get actual tac
            mov     b,#39
            mul     ab
            mov     a,r1
            add     a,b
            jc      ok1
            add     a,mpb+12
            jc      ok1
            cjne    a,12h,$+3               ; compare with r2
            jnc     ok1
ok2         mov     r2,a                    ; clamp @ 1.156 + TAC + mpb+12
ok1         mov     pwm0,r2
            mov     int,r4
            mov     int+1,r5
            pop     b
            pop     psw
            pop     acc
            reti ; COMMUTATE runs off the CT interrupt
; KK930701 commutate
            push    acc
            push    psw
c1          mov     a,p1                    ; 0 and 7 are invalid returns
            cjne    a,p1,c1
            anl     a,#7                    ; 3 phase mask
            xch     a,new                   ; save hall patterns
            xch     a,old
            cjne    a,new,c3                ; direction has changed if equal
            xrl     rotate,#0FFh            ; negate if direction changed
            inc     rotate
c3          jnb     lock.1,c6
            mov     a,posit
            jnz     c6
            clr     lock.1
            xrl     dir,#8
            setb    p0.5                    ; strobe pulse
c6          mov     a,new
            add     a,dir                   ; offset to data table
            movc    a,@a+pc                 ; get byte from table
            mov     pX,a                    ; output with 2 hi bits set
            mov     a,dtac
            inc     a
            jz      c7
            inc     dtac                    ; increment dynamic tac
```

A-7

```
c7      mov     a,posit
        add     a,rotate            ; track position
        jnb     acc.7,c4
        mov     a,mpb+9             ; fix underflow
        dec     a
        sjmp    c5
c4      cjne    a,mpb+9,c5
        clr     a                   ; fix overflow
c5      mov     posit,a             ; save shaft position
        pop     psw
        pop     acc
        reti cw      db      0FFh,0CBh,0ECh,0CEh,0F2h,0E3h,0F8h,0FFh ; commutation forward
        db      0FFh,0F8h,0E3h,0F2h,0CEh,0ECh,0CBh,0FFh ; commutation reverse
```

A-8

```
LOCK.0    REVERSE DIRECTION
    .1    REVERSE ON ZERO POSITION
    .2    JOG MODE
    .3    STOP
```

What is claimed is:

1. A surgical system adapted to operate with at least one surgical device, said surgical system having a handpiece containing a motor having a motor armature and adapted to receive and drive said surgical device, said surgical device being driven through a continuum of positions by said handpiece, said system comprising, a controller for controlling the driving of said surgical device, sensors in said motor for generating electrical signals indicative at least of a motor drive relative position, said controller being responsive to said relative position electrical signals for identifying a current position of said motor drive relative to the motor drive relative position, a position identifier for identifying to said controller a start-stop position for said driven surgical device for leaving said surgical device in a known condition, a stop switch electrically connected to said controller, and said controller being responsive to-actuation of said stop switch for stopping driven movement of said surgical device at substantially said start-stop position.

2. The surgical system of claim 1 wherein said position identifier comprises a manual switch, and said controller is responsive to actuation of said manual switch for marking the position of said driven surgical device at said start-stop position.

3. The surgical system of claim 1 wherein said position identifier comprises an electrical sensor element secured to said surgical device for causing generation of an electrical signal which identifies a device determinative position whenever said surgical device is positioned substantially at said determinative position, and said controller is responsive, at least to said generated electrical signal, for stopping driven movement said surgical device at substantially said start-stop position.

4. The surgical system of claim 3 wherein said electrical sensor element is attached to a driven member of said surgical device, and said system further comprises a receiving sensor attached to a fixed element member of said handpiece.

5. The surgical system of claim 3 wherein said electrical sensor element is attached to a driven member of said motor, said surgical device driven member cooperates with a surgical device non-driven member to effect surgical action, said motor includes a fixed receiving element aligned to the location of said electrical sensor element, and said motor and said surgical device interlock in a predetermined alignment for locating said device driven member relative to said electrical sensor element.

6. The surgical system of claim 4 wherein said fixed element member comprises a plurality of fixed receiving elements spaced circumferentially around the periphery of the handpiece for further identifying the type of driven member, said surgical device having a plurality of sensor elements for that purpose.

7. The surgical system of claim 1 wherein said controller further comprises means for tracking the position of said motor in response to said relative position electrical signals, said system further comprises a manual position switch, and said controller tracking means tracks the position of said motor armature relative to a position of said motor armature when said manual switch is actuated.

8. The surgical system of claim 1 wherein said controller controls said motor for two modes of operation, a continuous mode and an oscillatory mode, said controller is responsible to said stop switch, in both said continuous mode and said oscillatory mode for stopping driven movement of said surgical device at substantially said start-stop position, said controller, in said oscillatory mode, causing the driven movement of said surgical device to reverse at substantially said start-stop position.

9. The surgical system of claim 1 wherein said controller controls said motor for two modes of operation, a continuous mode and an oscillatory mode, and said controller is responsible to said stop switch, in both said continuous mode and said oscillatory mode for stopping driven movement of said surgical device at substantially said start-stop position, said position identifier being further able to identify a reverse position at which to reverse driven movement of said surgical device in said oscillatory mode, and said controller, in said oscillatory mode, causing the driven movement of said surgical device to reverse at substantially said reverse position.

10. The system of claim 9 wherein said start-stop position and said reverse position are the same.

11. The system of claim 1 wherein said surgical device comprises an arthroscopic surgical instrument adapted to be actuated by said motor to sever tissue at a surgical site in the body, said surgical device having a fixed elongate member, and a driven movable member, said fixed and movable members cooperatively arranged to effect severing of said tissue when said movable member is driven by said motor, said handpiece receiving a proximal portion of said surgical device, said surgical device, at its distal end, defining a variable aperture, which, depending upon the position of said movable member relative to said fixed member, can be fully open, fully closed, or partially open, whereby said surgical system can stop said movable member to provide a selectable degree of openness to said aperture.

12. The surgical system of claim 11 further wherein said movable member comprises at least one magnet embedded therein for effecting, in cooperation with said sensors, the generation of said electrical signals.

13. The surgical system of claim 11 further wherein said fixed member comprises at least one first relative position identifier, said movable member comprises a second relative position identifier, and said start-stop position identifier comprises a receiver sensor responsive to at least one of said first and second relative position identifiers for generating electrical signals for enabling said controller to operate in a closed loop fashion.

14. The surgical system of claim 13 wherein said first position identifier comprises a mechanical keying mechanism comprising a first key member at a proximal end of said surgical device fixed member, and a second key member at a drive element receiving section of said motor, and adapted to receive said first key member in a single relative position relationship.

15. The surgical system of claim 1 wherein said controller, in response to said actuation of said stop switch, decreases motor rotational speed in accordance with a predetermined procedure to stop said motor with said driven surgical device in substantially said known condition.

16. The surgical system of claim 1 wherein said controller, in response to said actuation of said stop switch, decreases motor rotational speed to less than a predetermined threshold value prior to bringing said motor to said stop with said surgical device in said known condition.

17. The surgical system of claim 1 wherein said handpiece further comprises a gear reducer for coupling an output movement of the motor to said surgical device, whereby a known position of the motor does not correspond to a single operative position of the surgical device.

18. The surgical system of claim 17 wherein said gear reducer has a gear reduction ratio which is an exact multiple of 1/ (number of Hall effect state changes per armature rotation).

19. The surgical system of claim 1 wherein said controller operates in an open loop control mode.

20. A method for operating a surgical system wherein the surgical system has a handpiece containing a motor which is adapted to receive a surgical device, the surgical device having a fixed member and a driven member, the fixed and the driven members cooperatively arranged to effect severing of tissue when the driven member is driven by said motor in said handpiece, and the handpiece receiving, at a distal end, a proximal end of the surgical device, the surgical device at its distal end defining a variable aperture, which, depending upon the position of the driven member relative to the fixed member can be fully open, fully closed, or partially open, and the surgical system having a control mechanism for controlling operation of the motor, the method comprising the steps of defining for the controller a stop position at which said driven member has a particular relationship to the fixed member; and starting and stopping said surgical device substantially at said stop position.

21. The method of claim 20 further comprising the steps of providing an electrical signal to the controller to tell the controller to stop said surgical device, reducing the speed of movement of the surgical device to below a threshold level, further reducing the speed of the surgical device in accordance with a defined speed reduction procedure to enable said motor to stop the surgical device at said stop position.

22. The method of claim 20 further comprising the steps of operating said motor in a continuous mode and in an oscillatory mode, and stopping said motor each time said motor reverses in said oscillatory mode substantially at said stop position.

23. The method of claim 20 further comprising the steps of operating said motor in a continuous mode and in an oscillatory mode, defining an oscillatory reversal position of said surgical device at which said oscillatory mode reverses direction, and reversing the direction of the motor in said oscillatory mode only substantially at said oscillatory mode reversal position, and stopping said motor when said system is in said oscillatory mode in response to a stop command at said stop position.

24. The method of claim 23 further comprising the step of driving said motor in one direction in said oscillatory mode for a fixed period of time.

25. The method of claim 24 wherein said fixed period of time is less than one second.

26. The method of claim 22 further comprising the step of driving said motor in one direction in said oscillatory mode for a fixed period of time.

27. The method of claim 26 wherein said fixed period of time is less than one second.

28. The method of claim 20 further comprising the steps of incrementally advancing said motor to a desired stop position of said surgical device; and recording said desired stop position of said surgical device as the stop position.

29. The method of claim 20 further comprising the step of controlling the rotation of said motor using an open loop control mode.

30. The method of claim 20 further comprising the step of controlling the rotation of said motor using a closed loop control mode.

* * * * *